United States Patent
Kuang et al.

(10) Patent No.: US 9,568,417 B2
(45) Date of Patent: Feb. 14, 2017

(54) SUPER-RESOLUTION MICROSCOPY METHOD AND DEVICE

(71) Applicant: ZHEJIANG UNIVERSITY, Hangzhou, Zhejiang Province (CN)

(72) Inventors: Cuifang Kuang, Hangzhou (CN); Shuai Li, Hangzhou (CN); Xiang Hao, Hangzhou (CN); Zhaotai Gu, Hangzhou (CN); Xu Liu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 124 days.

(21) Appl. No.: 14/411,373

(22) PCT Filed: Oct. 22, 2012

(86) PCT No.: PCT/CN2012/083320
§ 371 (c)(1),
(2) Date: Dec. 24, 2014

(87) PCT Pub. No.: WO2014/000351
PCT Pub. Date: Jan. 3, 2014

(65) Prior Publication Data
US 2015/0211986 A1    Jul. 30, 2015

(30) Foreign Application Priority Data

Jun. 29, 2012    (CN) .......................... 2012 1 0227898

(51) Int. Cl.
*G01J 4/00*    (2006.01)
*G01N 21/27*    (2006.01)
(Continued)

(52) U.S. Cl.
CPC ............ *G01N 21/27* (2013.01); *G01N 21/255* (2013.01); *G01N 21/6458* (2013.01);
(Continued)

(58) Field of Classification Search
CPC .. G01N 21/27; G01N 21/255; G01N 21/6458; G01N 2201/06113; G01N 2201/064; G02B 21/002; G02B 21/0032; G02B 21/0068; G02B 27/58
See application file for complete search history.

(56) References Cited

U.S. PATENT DOCUMENTS

| 5,963,314 A | * | 10/1999 | Worster | ............. | G01N 21/9501 |
| | | | | | 250/559.39 |
| 2008/0192337 A1 | * | 8/2008 | Osawa | ............... | G02B 21/0032 |
| | | | | | 359/370 |

(Continued)

FOREIGN PATENT DOCUMENTS

| CN | 101504490 A | 8/2009 |
| CN | 10185294 A | 10/2010 |

(Continued)

OTHER PUBLICATIONS

Pavani SRP, et al. Three-dimensional, single-molecule fluorescence imaging beyond the diffraction limit by using a double-helix point spread function.

(Continued)

*Primary Examiner* — Kara E Geisel
*Assistant Examiner* — Rufus Phillips
(74) *Attorney, Agent, or Firm* — Jiwen Chen (57) ABSTRACT

This invention discloses a super-resolution microscopy method and device, of which the method comprises the following steps: converting laser beam into linearly polarized light after collimation; linearly polarized light is deflected and phase modulated by a spatial light modulator; the deflected beam is focused, collimated and then converted into circularly polarized light for projection on the sample to collect signal light from various scanning points on the sample, and obtaining the first signal light intensity; switching over modulation function to project linearly polarized (Continued)

light modulated by the second phase modulation on the sample to collect signal light from various scanning points on the sample, and obtaining the second signal light intensity; calculating valid signal light intensity to obtain the super-resolution image. This device features in a simple structure and easy operation, which can obtain a super-resolution beyond diffraction limit at a lower luminous power; it is quick in image formation with the frame frequency over 15 frames when the number of scanning points in each image is 512×512.

2 Claims, 6 Drawing Sheets (51) Int. Cl.
G02B 21/00 (2006.01)
G01N 21/64 (2006.01)
G01N 21/25 (2006.01)
G02B 27/58 (2006.01)

(52) U.S. Cl.
CPC ....... *G02B 21/002* (2013.01); *G02B 21/0032* (2013.01); *G02B 21/0068* (2013.01); *G02B 27/58* (2013.01); *G01N 2201/064* (2013.01); *G01N 2201/06113* (2013.01)

(56) References Cited

U.S. PATENT DOCUMENTS

| 2011/0140000 A1* | 6/2011 | Iketaki | G02B 21/0068 250/458.1 |
| 2012/0026311 A1* | 2/2012 | Ouchi | G02B 21/06 348/79 |

FOREIGN PATENT DOCUMENTS

| CN | 102062572 A | 5/2011 |
| CN | 102735617 A | 10/2012 |

OTHER PUBLICATIONS

Proceedings of the National Academy of Sciences of the United States of America (PNAS): Mar. 3, 2009;106(9):2995-2999.

* cited by examiner

SUPER-RESOLUTION MICROSCOPY METHOD AND DEVICE

This is a U.S. national stage application of PCT Application No. PCT/CN2012/083320 under 35 U.S.C. 371, filed Oct. 22, 2012 in Chinese, claiming the priority benefit of Chinese Application No. 201210227898.7, filed Jun. 29, 2012, which is hereby incorporated by reference.

FIELD OF THE INVENTION

The present invention is related to the super-resolution field, in particular to a super-resolution method and device that can achieve super-resolution beyond diffraction limit at the far field.

BACKGROUND OF THE INVENTION

Due to the impact from diffraction of optical system, resolution obtained from conventional far-field microcopy method is limited. According to Abbe's diffraction limit theory, dimension of the light spot formed through focusing of the light beam by the microscope is indicated as $$\Delta r = \frac{\lambda}{2NA}$$

by using the full width at half maximum; wherein, $\lambda$ refers to the working wave length of the microscope; NA refers to the numerical aperture of the microscope used. Therefore, limiting resolution of conventional far-field optical microscope is normally restricted to about half wave length.

In recent years, scientific researchers have proposed numerous super-resolution microscopy methods in an attempt to break through restrictions of optical diffraction limit, and improve resolution ratio of the microscopy system.

For instance, the Stimulated Emission Depletion Microscopy (STED) makes use of the non-linear relationship between the fluorescence saturation and excited fluorescence excitation loss, restricts the area of excited radiation attenuation and reduces the size of the fluorescent light spot to obtain the luminous point below the diffraction limit, improve system resolution ratio, break through restriction on resolution by the diffraction limit of far-field microscopy, and achieve non-contact 3D imaging. Others include Structured Illumination Microscopy (SIM) and Stochastic Optical Reconstruction Microscopy (STORM), etc.

Despite of the fact that they all can achieve fluorescent super-resolution microscopy at the far field and obtain corresponding applications during practical tests, aforesaid several methods still have their own disadvantages. Among them, resolution for STED microscopy is determined by the light power consumed; therefore, the light power required in realization of high resolution is very strong, which is apt to incur bleaching to fluorescent molecules. Furthermore, STED microscopy system is relatively complicated, which is normally expensive. Despite of the fact that SIM microscopy has lower requirements for light power, it still requires raster scanning, which may result in relatively slower image formation and complicated image forming system. Image formation speed of STORM microscopy is also very slow, which is unlikely to be applied to real-time test of living cell at present.

SUMMARY OF THE INVENTION

The present invention provides a super-resolution method and device that can achieve the resolution of super diffraction limit at far field. Such method and device feature in quick speed of image formation, simple structure and high resolution, which can be effectively used to test fluorescent and non-fluorescent samples.

A super-resolution microscopy method, comprising the following steps:

1) Laser beam is converted into linearly polarized light through collimation;

2) The linearly polarized light's phase is modulated according to the modulation function $f_1(\rho,\phi)=0$, wherein, $\rho$ refers to the distance between a certain point on the beam and the optical axis; $\phi$ refers to the angle between the polar coordinate vector and axis x in the beam section which is vertical to optical axis;

3) Proceeding with optical deflection of the linearly polarized light through the phase modulation;

4) The deflected beam through focus and collimation is converted into circularly polarized light for projection on the sample to achieve 2D scanning of the sample;

5) Collecting signal light from various scanning points on the sample during 2D scanning, and eliminating the stray light to obtain the first signal light intensity $I_1$ (x, y); x, y refers to the 2D coordinate of the scanning point;

6) Switching over the modulation function in step 2) to $f_2(\rho,\phi)=\phi$; p refers to the distance between a certain point on the beam and the optical axis; $\phi$ refers to the angle between the polar coordinate vector and axis x in the beam section which is vertical to optical axis;

7) Repeating steps 3), and 4), and proceeding with second scanning of various scanning points in step 5) to collect the second signal light intensity $I_2$ (x,y);

8) Calculating valid signal light intensity I(x, y) based on the formula $I(x, y)=I_1(x, y)-\gamma I_2(x,y)$, and making use of I(x,y) to obtain the super-resolution image; wherein $$\gamma = \frac{I_1^{max}}{2I_2^{max}},$$

$I_1^{max}$ refers to the maximum value of the first signal light intensity $I_1$(x, y); $I_2^{max}$ refers to the maximum value of the second signal light intensity $I_2$(x, y).

When the sample to be tested is the fluorescent one, the signal light will be the fluorescent light stimulated by the circularly polarized light on the sample through projection by the microscope; when the sample to be tested is the non-fluorescent one, the signal light will be the reflected beam produced by the circularly polarized light on the surface of the sample following projection by the microscope.

Orientation of axis x and y on the sample is determined by 2D scanning orientation.

When the valid signal light intensity value I(x, y) is negative, I(x, y)=0 is set.

The present invention provides a super-resolution microscopy device comprising a light source, a sample table used to carry the sample and a microscope used to project the light beam to the sample table; the following devices are arranged in turn between the light source and the microscope:

The polarizer used to convert the light beam from the light source into linearly polarized light;

The spatial light modulator used for phase modulation of the linearly polarized light;

The scanning galvanometer system used for optical deflection of the light beam after phase modulation;

The scanning optical lens and field lens arranged in sequence for focus and collimation of the light beam from the scanning galvanometer system;

The ¼ wave plate used to convert the aligned light beam into circular polarized light; the circularly polarized light is projected to the sample via the microscope;

Furthermore, the controller used for control of the spatial light modulation and scanning galvanometer system as well as the detection system used to collect signal light from the sample are also provided.

The detection system comprises the following devices:

A beam splitter arranged between the spatial light modulator and the scanning galvanometer; the dichroic mirror is selected as the beam splitter when the sample is the fluorescent one; whereas polar beam splitter is selected when the sample is the non-fluorescent one;

A band filter used to eliminate the stray light in the signal light from the beam splitter; the band filter can be omitted when the sample is the non-fluorescent one;

A detector used to detect light intensity signal from the signal beam; the detector comprises a photomultiplier tube (PMT) or an avalanche photo diode (APD);

A focusing lens used to focus filtered signal beam on the detector;

A spatial filter, which is located at the focus plane of the focusing lens, is used for spatial wave filtration of the signal beam; the spatial filter can be provided with a pinhole or a multi-mode optical fiber; if the pinhole is provided, its diameter shall be smaller than the airy disk diameter.

A single-mode optical fiber and collimation lens for wave filtration and collimation are provided between the light source and polarizer in sequence.

The spatial light modulator is provided with a first modulation function $f_1(\rho,\phi)=0$ and a second modulation function $f_2(\rho,\phi)=\rho$ available for switchover; wherein, $\rho$ refers to the distance between a certain point on the beam and the optical axis; $\phi$ refers to the angle between the polar coordinate vector and axis x in the beam section which is vertical to the optical axis;

Switchover frequency of the two functions of spatial light modulator is the same as the frame scanning frequency of the scanning galvanometer system, which can guarantee the switchover of the modulation function of the spatial light modulator immediately following the scanning of the image by the galvanometer system.

In a preferred embodiment, NA, numerical aperture of the microscope is 1.4.

The present invention also provides a super-resolution microscopy device comprising a first light source, a second light source, a sample table used to carry the sample and a microscope used to project the light beam to the sample table, further comprising the following:

a first polarizer located on a first light route;

a second polarizer and a phase plate arranged on a second light route in sequence;

a scanning galvanometer system used for deflection of light beam on the first and second light routes;

scanning optical lens and field lens arranged in sequence for focus and collimation of the light beam from the scanning galvanometer system;

a ¼ wave plate used to convert the aligned light beam into circular polarized light; the circularly polarized light is projected to the sample via the microscope;

furthermore, a controller used for control of the first light source, the second light source and the scanning galvanometer system as well as the detection system used to collect signal light from the sample are also provided.

The detection system comprises the following devices:

a beam splitter arranged between the spatial light modulator and the scanning galvanometer; the dichroic mirror is selected when the beam splitter when the sample to be tested is the fluorescent one; whereas polar beam splitter is selected when the sample to be tested is the non-fluorescent one;

a band filter used to eliminate the stray light in the signal light from the beam splitter; the band filter can be omitted when the sample is the non-fluorescent one;

a detector used to detect light intensity signal from the signal beam; the detector comprises a photomultiplier tube (PMT) or an avalanche photo diode (APD);

a focusing lens used to focus filtered signal beam on the detector;

a spatial filter, which is located at the focus plane of the focusing lens, is used for spatial wave filtration of the signal beam; the spatial filter can be provided with a pinhole or a multi-mode optical fiber; if the pinhole is provided, its diameter shall be smaller than the airy disk diameter.

A first single-mode optical fiber and a first collimation lens are provided between the first light source and the first polarizer in proper sequence; whereas a second single-mode optical fiber and a second collimation lens are provided between the second light source and the second polarizer in proper sequence.

The modulation function of the phase plate is $f_3(\rho,\phi)=\phi$, wherein, $\rho$ refers to the distance between a certain point on the beam and the optical axis; $\phi$ refers to the angle between the polar coordinate vector and axis x in the beam section which is vertical to optical axis.

In a preferred embodiment, NA, numerical aperture of the microscope is 1.4.

The principles of the present invention are stated as follows:

Affected by diffraction of the optical system, the light spot focused by a parallel illuminating beam through the microscope on the sample is a diffraction spot of certain size rather than an ideal spot. Any sample within the radiation scope of diffraction spot may produce corresponding signal light to make it impossible to identify details of samples within this scope, which restrict resolution of the microscopy system. Therefore, the approach to reduce the emitting area of valid signal light at the scanning point serves as a critical link for breakthrough of restrictions by the optical diffraction limit and improvement of resolution of the microscopy system.

According to the method of the present invention, it is calculated with Debye integral that the light spot produced on the sample through focusing of modulated beam by the microscope is a solid light spot when the modulation function of spatial light modulator is $f_1(\rho,\phi)=0$. The size of such solid light spot is the same as that of the diffraction spot focused by illuminating light used for conventional microscopy. Signal light from samples within the radiation scope of such solid light spot is collected by the detector to obtain the first signal light intensity $I_1$ at the current scanning point; when modulation function of spatial light modulator is $f_2(\rho,\phi)=\phi$, it can be calculated with Debye integral that the light spot formed on the sample focused by the modulated beam by the microscope is a bagel shaped hollowed light spot. Signal light from the periphery of such light spot is collected by the detector to obtain the second signal light intensity $I_2$. $I(x, y)$ is obtained through calculation with formula $I(x, y)=I_1(x, y)-\gamma I_2(x, y)$; it is obvious that lighting area of valid signal light at each scanning point corresponding to $I(x, y)$ is below that of the first signal light at each scanning point corresponding to $I_1(x,y)$. Therefore, as compared with conventional microscopy methods, the present invention can achieve the resolution of super diffraction limit by reducing the lighting area of valid signal light.

As compared with prior arts, the present invention is provided with the following beneficial technical effects:

(1) Achieving super-resolution beyond diffraction limit under lower light power;

(2) Quick image formation: Frame frequency is up to 15 frames per second when the scanning point is 512×512 for each image;

(3) Simple structure and easy operation.

PREFERRED EMBODIMENTS OF THE INVENTION

The present invention is described in detail as follows in combination with embodiments and drawings; however, the present invention is not limited to this scope.

Figure 1:
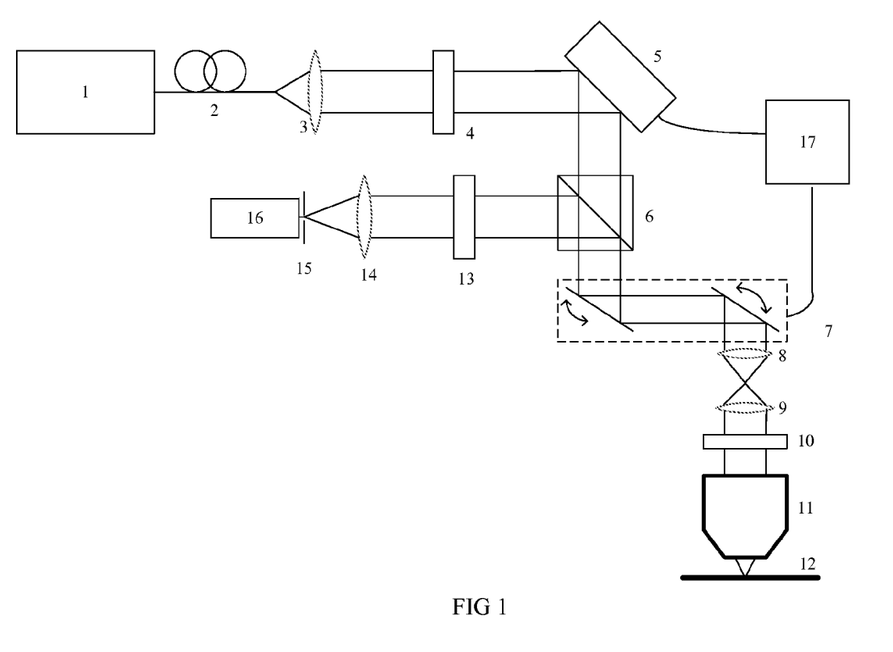
FIG. 1 is a diagram for a super-resolution microscopy device of the present invention.

As shown in FIG. 1, a super-resolution device comprising a laser 1, a single-mode optical fiber 2, a collimation lens 3, a polarizer 4, a spatial light modulator 5, a beam splitter 6, a scanning galvanometer system 7, a scanning lens 8, a field lens 9, a ¼ wave plate 10, a microscope 11, a sample table 12, a band filter 13, a focusing lens 14, a pinhole 15, a detector 16 and a controller 17.

Wherein, the single-mode optical fiber 2, the collimation lens 3, the polarizer 4 and the spatial light modulator 5 are located on the optical axis of outgoing beam of the laser 1 in proper sequence; transparent axis of the polarizer 4 is parallel to the horizontal orientation.

Wherein, the beam splitter 6 and the scanning galvanometer system 7 are located on the optical axis of the beam modulated by the spatial light modulator 5 in sequence.

Wherein, the scanning lens 8, the field lens 9, the ¼ wave plate 10, the microscope 11 and the sample table 12 are located on the optical axis of outgoing beam of the scanning galvanometer 7; the sample 12 is located near the focus plane of the microscope 11.

Wherein, the band filter 13, the focusing lens 14, the pinhole 15 and the detector 16 are located on the optical axis of reflected beam of the beam splitter 6; the pinhole 15 is located on the focus plane of the focusing lens 14.

Wherein, the controller 17 is connected with the spatial light modulator 5 and the scanning galvanometer system 7, respectively, to control switchover of the spatial light modulator 5 and scanning of the scanning galvanometer 7; controlled by the controller 17, the spatial light modulator 5 is available for switchover between the following two modulation functions as represented by $f_1(\rho,\phi)=0$ and $f_2(\rho,\phi)=\phi$ at the specified switching frequency; wherein, $\rho$ refers to the distance between a certain point on the beam and the optical axis; $\phi$ refers to angle between the polar coordinate vector and axis x in the beam section which is vertical to optical axis; switching frequency of the spatial light modulator 5 is identical to the frame scanning frequency of the scanning galvanometer system 7, which can guarantee the switchover of the modulation function of the spatial light modulator 5 immediately following the scanning of the image by the galvanometer system 7.

In the aforesaid devices, NA, numerical aperture of microscope 11 is 1.4; diameter of the pinhole 15 used is equivalent to 0.73 Airy disc diameter; avalanche photo diode (APD) is used as the detector 16.

The method for super-resolution microscopy using the device as shown in FIG. 1 is stated as follows:

A laser beam from the laser 1 is to be transmitted to single-mode optical fiber 2 firstly; whereas laser beam from single-mode optical fiber 2 is to be collimated by collimation lens 3. The collimated beam transmitted to the polarizer 4 is to be converted into linearly polarized light for further transmission to the spatial light modulator 5 for phase modulation.

Making use of controller 17 to control spatial light modulator 5 to switch over phase modulation function to $f_1(\rho,\phi)=0$.

Wherein, $\rho$ refers to the distance between a certain point on the beam and the optical axis; $\phi$ refers to angle between the polar coordinate vector and axis x in the beam section which is vertical to optical axis.

Therefore, electric vector intensity of outgoing beam through phase modulation by spatial light modulator 5 can be indicated with the following formula:

$$E_1(\rho,\phi)=E_0(\rho,\phi)\exp[if_1(\rho,\phi)]=E_0(\rho,\phi)$$

Wherein, $E_0(\rho,\phi)$ refers to the electric vector intensity of the beam transmitted to spatial light modulator 5 at $(\rho,\phi)$; $E_1(\rho,\phi)$ refers to the electric vector intensity of outgoing beam through phase modulation at $(\rho,\phi)$ by spatial light modulator 5; i is an imaginary unit.

The beam from the spatial light modulator 5 is to pass through beam splitter 6 to scanning galvanometer system 7. The beam from scanning galvanometer system 7 is to be subject to focusing by the scanning lens 8 and collimation by the field lens 9 before being converted into circularly polarized light by the ¼ wave plate 10; the circularly polarized light is to be projected by the microscope 11 on the sample on sample table 12.

Distribution of light field formed by the incoming circularly polarized light near the focus of microscope 11 can be determined by Debye's integral as follows:

$$\vec{E}(r_2,\phi_2,z_2)= iC\int\int_\Omega \sin(\theta)\cdot A_1(\theta,\phi)\cdot A_2(\theta,\phi)\cdot\begin{bmatrix}p_x\\p_y\\p_z\end{bmatrix}\cdot e^{ikn(z_2\cos\theta+r_2\sin\theta\cos(\phi-\phi_2))}d\theta d\phi$$

In the formula, $(r_2,\phi_2,z_2)$ refers to cylindrical coordinate system taking the focus of the microscope 11 as an original point; $\vec{E}(r_2,\phi_2,z_2)$ refers to electric vector intensity at $(r_2,\phi_2,z_2)$; i is an imaginary unit; C refers to normalization constant; $\theta$ refers to beam aperture angle; $\phi$ refers to the angle between the polar coordinate vector and axis x in the beam section which is vertical to axis z; $A_1(\theta,\phi)$ refers to the amplitude distribution of incoming light; $A_2(\theta,\phi)$ refers to the structure of microscope 11;

$$\begin{bmatrix} p_x \\ p_y \\ p_z \end{bmatrix}$$

refers to polarization information of incoming light; $k=2\pi/\lambda n$ refers to medium refraction index.

Figure 2:
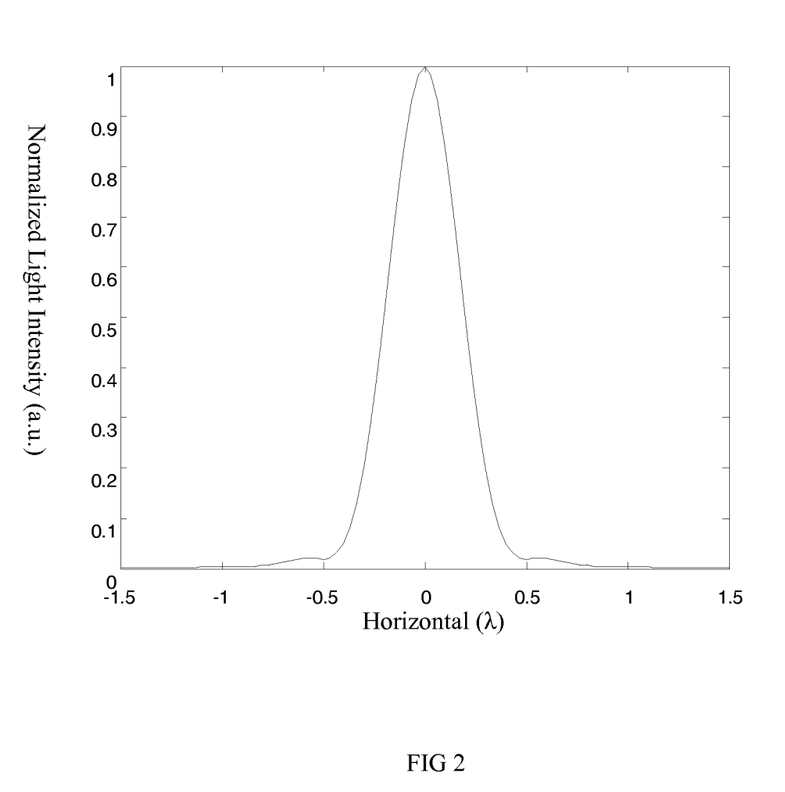
FIG. 2 is a normalized light intensity distribution curve for the solid light spot of the present invention.

As calculated with aforesaid formula, the light spot formed by incoming circularly polarized light on the sample through focusing by the microscope 11 is a solid one; normalized curve for the distribution of its specific light field is shown in FIG. 2.

The signal light from the sample is collected by the microscope 11 before passing through the ¼ wave plate 10, the field lens 9, the scanning lens 8 and the scanning galvanometer system 7, which is to be eventually reflected by the beam splitter 6. The signal beam reflected by the beam splitter 6 passes through the band filter 13 to eliminate stray light; after that, it is subject to focusing by the focusing lens 14 and spatial wave filtration by the pinhole 15, which is to be eventually detected by the detector 16. Signal light intensity detected by the detector 16 at this point is recorded as $I_1$, which serves as the first signal light intensity at the current scanning point.

Using the controller 17 to regulate scanning galvanometer system 7 to achieve 2D scanning of the sample, and record the first signal light intensity $I_1(x, y)$ at each scanning point; wherein, x, y refers to 2D coordination at the scanning point.

Using the controller 17 to control spatial light modulator 5 to switch over phase modulation function to $f_2(\rho,\phi)=\phi$;

wherein, $\rho$ refers to the distance between a certain point on the beam and the optical axis; $\phi$ refers to refers to angle between the polar coordinate vector and axis x in the beam section which is vertical to optical axis.

At this point, electric vector intensity of outgoing beam following phase modulation by spatial light modulator 5 can be indicated with the following formula:

$$E_2(\rho,\phi)=E_0(\rho,\phi)\exp[if_2(\rho,\phi)]=E_0(\rho,\phi)\exp(i\phi)$$

wherein, $E_0(\rho,\phi)$ refers to electric vector intensity of the beam on the spatial light modulator 5 at $(\rho,\phi)$; $E_2(\rho,\phi)$ refers to electric vector intensity of outgoing beam at $(\rho,\phi)$ following modulation by the spatial light modulator 5; i is an imaginary unit.

The beam from the spatial light modulator 5 is to pass through the beam splitter 6 to the scanning galvanometer system 7. The beam from the scanning galvanometer system 7 is focused by the scanning lens 8 and collimated by the field lens 9 respectively before being converted into circularly polarized light by the ¼ wave plate 10. The circularly polarized beam is to be projected by the microscope 11 to the sample on the sample table 12.

Figure 3:
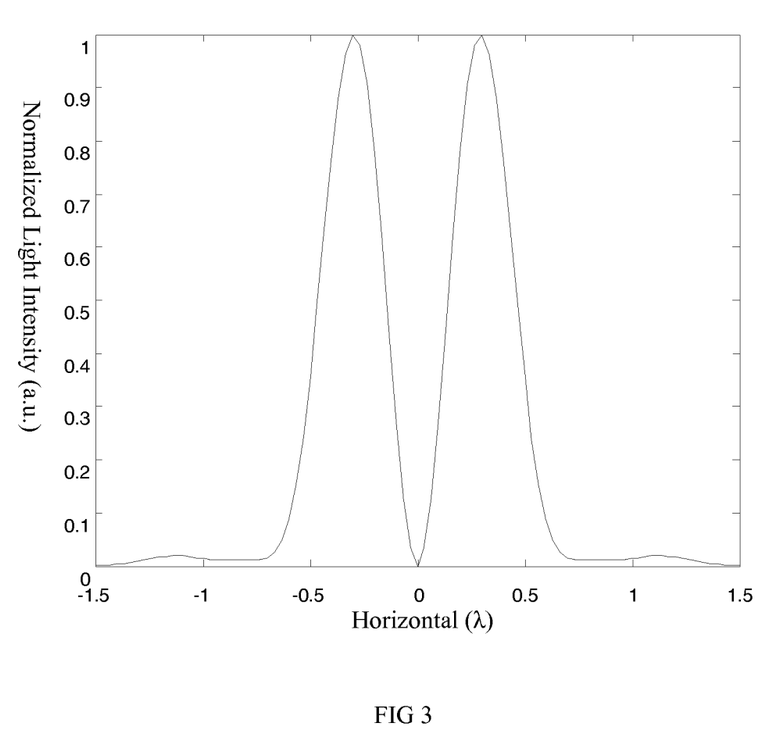
FIG. 3 is a normalized light intensity distribution curve for the bagel shaped hollowed light spot of the present invention.

The distribution of light field formed by the incoming circularly polarized light near the focus of the microscope 11 can also be determined by Debye's integral. Through calculation, it can be discovered that the light spot formed on the sample by incoming circularly polarized light through focusing by the microscope 11 is a bagel shaped hollowed light spot; normalized curve for its light field is shown in FIG. 3.

The signal light from the sample is collected by the microscope 11 before passing through the ¼ wave plate 10, the field lens 9, the scanning lens 8 and the scanning galvanometer system 7 in turn, which is to be eventually reflected by the beam splitter 6. The signal beam reflected by the beam splitter 6 will pass through the band filter 13 to eliminate stray light; after that, it will be subject to focusing by the focusing lens 14 and spatial wave filtration by the pinhole 15, which is to be eventually detected by the detector 16. The signal light intensity detected by the detector 16 at this point is recorded as $I_2$, which serves as the second signal light intensity at the current scanning point.

The controller 17 is used to regulate the scanning galvanometer system 7 to achieve 2D scanning of the sample; record the second signal light intensity $I_2(x, y)$ at each scanning point; wherein, x, y refers to 2D coordinate of the scanning point.

The formula $I(x, y)=I_1(x, y)-\gamma I_2(x, y)$ is used to calculate valid signal light intensity $I(x, y)$ at each scanning point to obtain the super-resolution microscopy image eventually.

Figure 4:
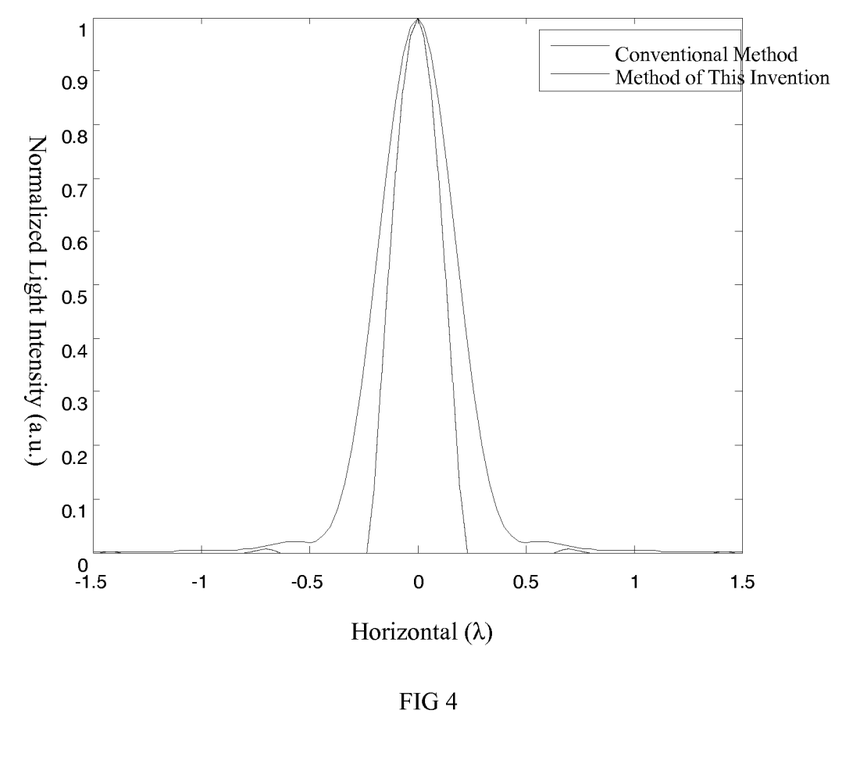
FIG. 4 is a normalized light intensity distribution curve for light spot of valid signal light in the present invention and signal light of conventional microscopy.

A comparison of normalized light intensity distribution curve for valid signal light spot of the present invention and that of conventional confocal microscopy is shown in FIG. 4. From FIG. 4, it can be seen that light spot size (full width at half maximum is 0.34 wave length) of valid signal light of the present invention is somehow reduced as compared with signal light spot size (full width at half maximum is 0.41 wave length) of conventional confocal microscopy; on this account, the method of the present invention can achieve resolution of super diffraction limit.

Figure 5:
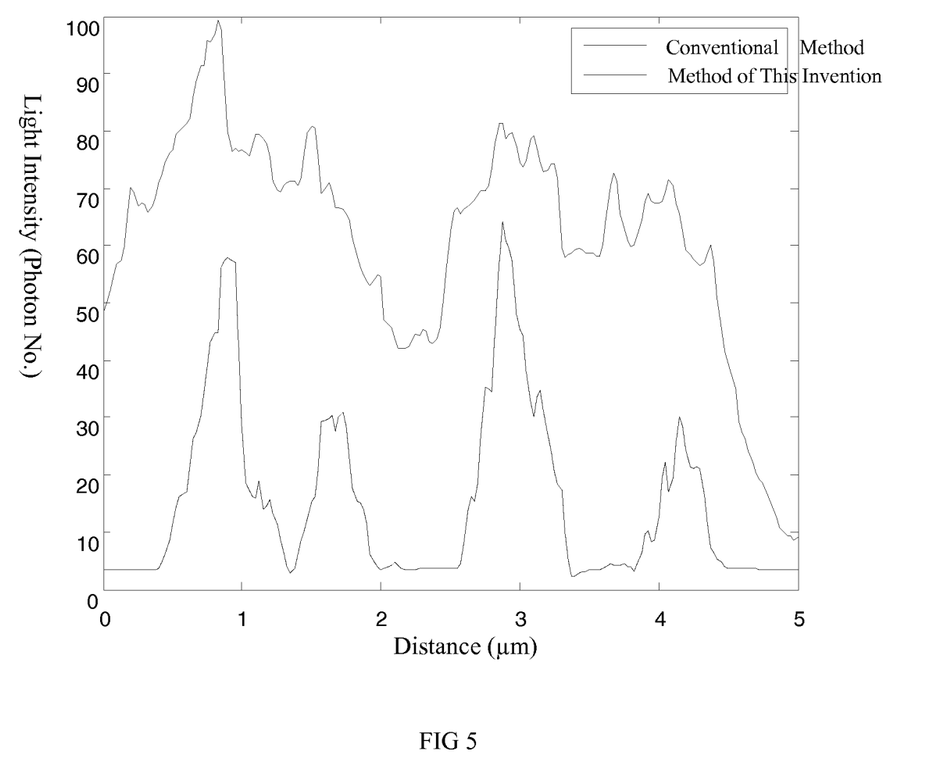
FIG. 5 is a light intensity distribution curve for images formed through scanning of the same sample with the method of the present invention and conventional optical microscopy methods.

To verify resolving power of the method in the present invention, scanning image for the same sample is obtained with the method of the present invention and conventional confocal microscopy respectively; a comparison of specific light intensity curve is shown in FIG. 5. The samples are four fluorescent particles in compact arrangement; the diameter of such fluorescent particles is 100 nanometers.

From FIG. 5, it can be seen that in the scanning image obtained through conventional confocal microscopy, point spread functions of the fluorescent light from fluorescent particles are mutually overlapped, which are unable to be identified. On the contrary, in the scanning image obtained with the method of the present invention, 4 peaks are obvious, and 4 fluorescent particles can be easily identified.

Figure 6:
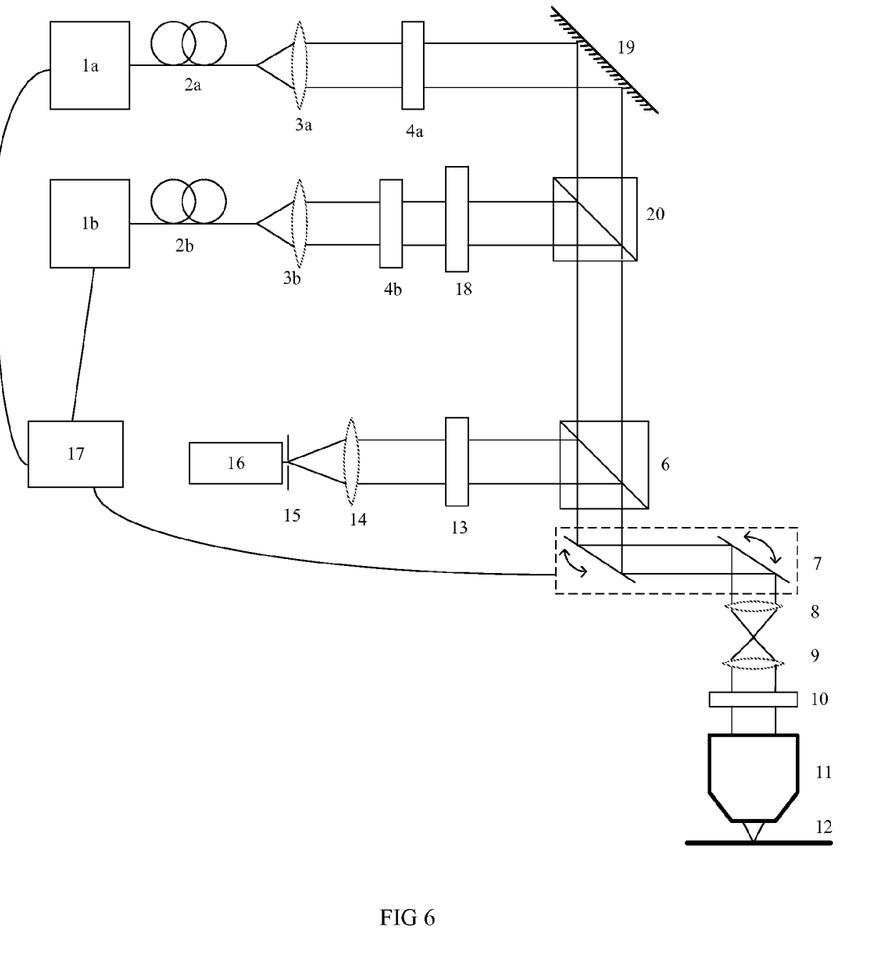
FIG. 6 is a diagram for realization of device with the method of the present invention by using two lasers.

A super-resolution microscopy device of the present invention can also be achieved by two lasers as shown in FIG. 6. As compared with the device using a single laser, the device using two lasers has replaced the spatial light modulator 5 with the reflector mirror 19 while increasing a second laser 1b, a second single-mode optical fiber 2b, a second collimation lens 3b, a second polarizer 4b, a phase plate 18 and a polarizing beam splitter 20; furthermore, the controller 17 is connected with the first laser 1a, second laser 1b and scanning galvanometer system 7 respectively to control opening and closure of the first laser 1a and the second laser 1b as well as scanning of the scanning galvanometer system 7.

Wherein, the second laser 1b is identical to the laser 1a.

Wherein, the reflector mirror 19 is used for reflex of light route; the beam reflected by it is to be vertically transmitted to the top of the polarizing beam splitter 20.

Wherein, transmission axis of the second polarizer 4b is vertical to horizontal orientation.

Wherein, the phase plate 18 is a 0·2π vortex one, whose phase modulation function is stated as follows:

$$f_3(\rho,\phi)=\phi$$

Wherein, $\rho$ refers to the distance between a certain point on the beam and the optical axis; $\phi$ refers to the angle between the polar coordinate vector and axis x in the beam section which is vertical to optical axis.

The method for super-resolution microscopy by using the device shown in FIG. 6 is stated as follows:

Using the controller 17 to turn on the first laser 1a, and turn off the second laser 1b.

The laser beam from laser 1a is to be transmitted to the single-mode optical fiber 2a firstly; whereas the laser beam from first single-mode optical fiber 2a is to be collimated by the collimation lens 3a. The collimated beam transmitted to the first polarizer 4a is to be converted into linearly polarized light for further transmission to the reflector mirror 19 for light route reflex.

The beam reflected by the reflector mirror 19 is to pass through the polarizing beam splitter 20 and beam splitter 6 before being transmitted to the scanning galvanometer system 7. The beam from the scanning galvanometer system 7 is to be subject to focusing by the scanning lens 8 and collimation by the field lens 9 before being converted into circularly polarized light by ¼ wave plate 10; the circularly polarized light is to be projected by the microscope 11 on the sample on the sample table 12.

The light field formed by the incoming circularly polarized light near the focus of the microscope 11 can be determined by Debye's integral. As calculated with aforesaid formula, the light spot formed by incoming circularly polarized light on the sample through focusing by the microscope 11 is a solid one; distribution of its light field is the same as the light spot as shown in FIG. 2.

The signal light from the sample is to be collected by the microscope 11 before passing through the ¼ wave plate 10, field lens 9, scanning lens 8 and scanning galvanometer system 7, which is to be eventually reflected by the beam splitter 6. The signal beam reflected by the beam splitter 6 will pass through the band filter 13 to eliminate stray light; after that, it will be subject to focusing by the focusing lens 14 and spatial wave filtration by the pinhole 15, which is to be eventually detected by the detector 16. The signal light intensity detected by the detector 16 at this point is recorded as $I_1$, which serves as the first signal light intensity at the current scanning point.

The controller 17 is used to regulate the scanning galvanometer system 7 to achieve 2D scanning of the sample; record the first signal light intensity $I_1(x,y)$ at each scanning point; wherein, x, y refers to 2D coordinate at the scanning point.

The controller 17 is used to turn off the first laser 1a, and turn on the second laser 1b simultaneously.

The laser beam from the second laser 1b is to be transmitted to the second single-mode optical fiber 2b firstly; whereas the laser beam from the second single-mode optical fiber 2b is to be collimated by the second collimation lens 3b. The collimated beam transmitted to the second polarizer 4b is to be converted into linearly polarized light for phase modulation by the phase plate 18.

The phase modulation function of phase plate 18 is stated as follows:

$$f_3(\rho,\phi)=\phi$$

wherein, $\rho$ refers to the distance between a certain point on the beam and the optical axis; $\phi$ refers to the angle between the polar coordinate vector and axis x in the beam section which is vertical to optical axis.

Therefore, the electric vector intensity of outgoing beam through phase modulation by the phase plate 18 can be indicated with the following formula:

$$E_3(\rho,\phi)=E_0(\rho,\phi)\exp[if_3(\rho,\phi)]=E_0(\rho,\phi)\exp(i\phi)$$

Wherein, $E_0(\rho,\phi)$ refers to the electric vector intensity of the beam on the phase plate 18 at $(\rho,\phi)$; $E_3(\rho,\phi)$ refers to electric vector intensity of outgoing beam at $(\rho,\phi)$ through phase modulation by the phase plate 18; i is an imaginary unit.

The beam from the phase plate 18 is to be reflected by the polarizing beam splitter 20 before being transmitted to the scanning galvanometer system 7 from the beam splitter 6. The beam from the scanning galvanometer system 7 is to be subject to focusing by scanning lens 8 and collimation by the field lens 9 respectively before being converted into circularly polarized light by the ¼ wave plate. The circularly polarized beam is to be projected by the microscope 11 to the sample on the sample table 12.

The distribution of light field formed by the incoming circularly polarized light near the focus of the microscope 11 can also be determined by Debye's integral. As discovered through calculation, the light spot formed on the sample by incoming circularly polarized light through focusing by the microscope 11 is a bagel shaped hollowed light spot; distribution of its light field is the same as the light spot as shown in FIG. 3.

The signal light from the sample is to be collected by the microscope 11 before passing through 1 teh/4 wave plate 10, field lens 9, scanning lens 8 and scanning galvanometer system 7 in turn, which is to be eventually reflected by the beam splitter 6. The signal beam reflected by the beam splitter 6 will pass through the band filter 13 to eliminate stray light; after that, it will be subject to focusing by focusing lens 14 and spatial wave filtration by the pinhole 15, which is to be eventually detected by the detector 16. Signal light intensity detected by the detector 16 at this point is recorded as $I_2$, which serves as the second signal light intensity at the current scanning point.

The controller 17 is used to regulate scanning galvanometer system 7 to achieve 2D scanning of the sample; record the second signal light intensity $I_2(x, y)$ at each scanning point; wherein, x, y refers to 2D coordinate of the scanning point.

The formula $I(x, y)=I_1(x, y)-\gamma I_2(x, y)$ is used to calculate valid signal light intensity $I(x, y)$ at each scanning point to obtain the super-resolution microscopy image eventually.

The invention claimed is:

1. A super-resolution microscopy method, characterized in that it comprises the following steps:
   1) converting a laser beam into a linearly polarized light after collimation;
   2) modulating the linearly polarized light's phase according to a modulation function $f_1(\rho,\phi)=0$, wherein, $\rho$ refers to a distance between a certain point on a beam and an optical axis; $\phi$ refers to an angle between a polar coordinate vector and axis x in a beam section which is vertical to the optical axis;
   3) proceeding with optical deflection of the linearly polarized light through phase modulation;
   4) focusing, collimating and converting deflected beam into circularly polarized light for projection on a sample to achieve 2D scanning of the sample;
   5) collecting signal light from various scanning points on the sample during 2D scanning, and eliminating stray light to obtain a first signal light intensity $I_1(x,y)$; x,y refers to 2D coordinate of the scanning point;
   6) switching over modulation function in step 2) to $f_2(\rho,\phi)=\phi$; $\rho$ refers to the distance between a certain point on the beam and the optical axis; $\phi$ refers to the angle between the polar coordinate vector and axis x in the beam section which is vertical to the optical axis;

7) repeating step 3), and step 4), and proceeding with second scanning of various scanning points in step 5) to collect a second signal light intensity $I_2(x,y)$;
8) calculating valid signal light intensity $I(x, y)$ based on the formula $I(x, y)=I_1(x,y)-\gamma I_2(x,y)$, and using $I(x,y)$ to obtain a super-resolution image; wherein, $$\gamma = \frac{I_1^{max}}{2I_2^{max}},$$

$I_1^{max}$ refers to a maximum value of the first signal light intensity $I_1(x,y)$; $I_2^{max}$ refers to a maximum value of the second signal light intensity $I_2(x, y)$.

2. The super-resolution microscopy method as claimed in claim 1, characterized in that when the valid signal light intensity value $I(x, y)$ is negative, setting $I(x, y)=0$.

* * * * *